(12) United States Patent
Kobayashi et al.

(10) Patent No.: US 9,327,050 B2
(45) Date of Patent: *May 3, 2016

(54) HEMOSTATIC MATERIAL CONTAINING NANO-FIBER CONTAINING SYNTHETIC COLLAGEN

(71) Applicant: JNC CORPORATION, Tokyo (JP)

(72) Inventors: Hisatoshi Kobayashi, Ibaraki (JP); Dohiko Terada, Ibaraki (JP); Masami Todokoro, Kanagawa (JP); Akiko Shimatani, Kanagawa (JP); Yukinori Kataoka, Shiga (JP)

(73) Assignee: JNC CORPORATION, Tokyo (JP)

( * ) Notice: Subject to any disclaimer, the term of this patent is extended or adjusted under 35 U.S.C. 154(b) by 57 days.

This patent is subject to a terminal disclaimer.

(21) Appl. No.: 13/848,737

(22) Filed: Mar. 22, 2013

(65) Prior Publication Data

US 2013/0251780 A1  Sep. 26, 2013

(30) Foreign Application Priority Data

Mar. 23, 2012 (JP) ................................. 2012-067629

(51) Int. Cl.
*A61L 26/00* (2006.01)
*A61K 38/00* (2006.01)
*A61L 15/22* (2006.01)

(52) U.S. Cl.
CPC ............ *A61L 26/0052* (2013.01); *A61L 15/225* (2013.01); *A61L 26/0066* (2013.01); *A61L 2400/04* (2013.01); *A61L 2400/12* (2013.01)

(58) Field of Classification Search
CPC ............ A61L 26/0052; A61L 26/0066; A61L 15/225; A61L 2400/04; A61L 2400/12; C08L 89/06
See application file for complete search history.

(56) References Cited

U.S. PATENT DOCUMENTS

2007/0224251 A1* 9/2007 Tanihara et al. ............... 424/445
2008/0260794 A1* 10/2008 Lauritzen ............... A61K 38/39
  424/423
2009/0299034 A1 12/2009 Cejas et al.

FOREIGN PATENT DOCUMENTS

| JP | 07118157 A | * 5/1995 | ........... A61K 31/765 |
| JP | 2003-321500 | 11/2003 | |
| JP | 2005-074079 | 3/2005 | |
| JP | 2005058499 A | * 3/2005 | .............. A61L 27/00 |
| WO | 2008075589 | 6/2008 | |

OTHER PUBLICATIONS

Collagen-*Homo sapiens*, from http://www.ncbi.nlm.nih.gov/protein/BAA04809.1, pp. 1-3, accessed Apr. 2, 2014.*
Machine translation of JP 2005-058499 A, pp. 1-31, accessed Apr. 1, 2014.*
Machine translation of JP 07118157 A, pp. 1-8, accessed Apr. 1, 2014.*
Zahedi et al, A review on wound dressings with an emphasis on electrospun nanofibrous polymeric bandages, Polym. Adv. Technol., 2010, 21, pp. 77-95.*
Gliomedin-isoform, from http://www.ncbi.nlm.nih.gov/protein/EAW77419.1, pp. 1-3, accessed Apr. 1, 2014.*
Cotton, from http://cottontoday.cottoninc.com/sustainability-about/cotton-vs-other-fibers/, p. 1, accessed Dec. 1, 2014.*
Definition of polymer, from www.biology-online.org/bodict/index.php?title=Polymer&printable=yes&printable=yes, p. 1, accessed Apr. 2, 2014.*
"Office Action of Japanese Counterpart Application", issued on Oct. 27, 2015, with partial English translation thereof, pp. 1-6.

* cited by examiner

*Primary Examiner* — Julie Ha
*Assistant Examiner* — Li Ni Komatsu
(74) *Attorney, Agent, or Firm* — Jianq Chyun IP Office

(57) ABSTRACT

A hemostatic material as a high-performance medical material is described, which is capable of stopping bleeding in short time and is easy to handle and produce. The hemostatic material contains a nano-fiber that contains: a polymer, and a polypeptide having a peptide fragment represented by formula (1):

$$-(\text{Pro-Y-Gly})_n- \quad (1)$$

wherein Y represents hydroxyproline or proline, and n represents an integer ranging from 5 to 9000.

5 Claims, 7 Drawing Sheets (a)

(b)

(a)

A view of peeling off the Al foil to expose the surface of the E-spun mat (b)

(a)
 (c)
 (b)
 (d)

(a)

(c)

(b)

(a)

(c)

(b)

HEMOSTATIC MATERIAL CONTAINING NANO-FIBER CONTAINING SYNTHETIC COLLAGEN

CROSS-REFERENCE TO RELATED APPLICATIONS

This application claims the priority benefit of Japan Application No. 2012-067629, filed on Mar. 23, 2012. The entirety of the above-mentioned patent application is hereby incorporated by reference herein and made a part of this specification.

BACKGROUND OF THE INVENTION

1. Field of Invention

This invention relates to a hemostatic material, and particularly to a hemostatic material that contains a nano-fiber containing a synthetic collagen.

2. Description of Related Art

A fiber having a nanometer-scale diameter (1 nm to 1000 nm) exhibits different material properties as compared to fibers having micrometer-scale or larger diameters, and is generally called a nano-fiber to distinguish from other fibers. For a nano-fiber has a very large surface area per unit weight, that is, a very large specific surface area, its applications in carrier materials of functional molecules, fluid-contact reaction materials, cloth materials, industrial material products, living material products, environmental material products, electrodes and membranes of fuel cells and rechargeable batteries, regenerative medicine materials, ultrahigh-performance filters, electronic papers, wearable cells, protective clothing and so on have been investigated, and the studies and developments thereof in the respective fields have been extensively conducted. Moreover, the affects of nano-fiber materials to cells, etc. have received a lot of attention, and there are numerous reports on the studies of medical materials utilizing nano-fibers.

Currently, collagen, being a type of protein, is widely used as a general medical material. The natural type-one collagen molecule has a characteristic primary structure formed by a repetition of three amino-acid residues, Gly-X-Y, wherein X and Y are selected from various amino acids; but in most cases, X is Pro and Y is Hyp. Three chains of the polypeptide having the same orientation together constitute a triple-helix tertiary structure and form a collagen fiber.

On the other hand, a synthetic collagen molecule, which was created as a collagen-like peptide and is formed by a repetition of three amino-acid residues, Pro-Y-Gly (Y is proline or hydroxyproline), has also been reported to have a triple helix structure, and has been studied as various functional materials, as described in Patent Document 1.

Particularly, Patent Document 2 has reported a sponge-like hemostatic material, which is obtained by freeze-drying a hemostatic material that contains thrombin and a synthetic collagen containing a peptide unit represented by Pro-Y-Gly.

However, the hemostatic material disclosed in Patent Document 2 contains, as an essential component, thrombin that is a blood coagulation factor, and the hemostatic function of the synthetic collagen itself is unknown. Moreover, the operatability and the productivity of the hemostatic material are also desired to be improved.

The nano-fiber formed from the synthetic collagen can be made into a highly functional material or a multi-functional material by controlling the sequence of the amino acid residues and also utilizing the chemical modifiability and so on of the amino acid residues. Moreover, when such nano-fiber is used as the raw material of a hemostatic material, the operatability is improved.

However, different from the case of the natural collagen, such synthetic collagen has a poor interaction between its high-molecular peptide chains because of the simple repetition structure formed from Pro-Y-Gly only, and exhibits a high solubility in water. Hence, a long fiber like the natural collagen fiber still cannot be formed currently.

PRIOR-ART DOCUMENTS

Patent Documents

[Patent Document 1] International Patent Publication No. WO 2008/075589
[Patent Document 2] Japan Patent Publication No. 2005-074079

SUMMARY OF THE INVENTION

In view of the foregoing, this invention provides a hemostatic material that has a high hemostatic effect and improved operatability and productivity by incorporating a synthetic collagen into a nano-fiber.

After a diligent study of the above issues, the Inventors have succeeded in incorporating a synthetic collagen into a nano-fiber through electro-spinning of the synthetic collagen and a polymer. This invention is accomplished by using such nano-fiber as the raw material of a hemostatic material.

Specifically, this invention includes the following items.

Item [1] is a hemostatic material, which comprises a nano-fiber that comprises: a polymer, and a polypeptide having a peptide fragment represented by formula (1):

$$\text{-(Pro-Y-Gly)}_n\text{-} \tag{1}$$

wherein Y represents hydroxyproline or proline, and n represents an integer ranging from 5 to 9000.

Item [2] is the hemostatic material of [1], wherein the content of the polypeptide in the nano-fiber ranges from 2.5 wt % to 90 wt %.

Item [3] is the hemostatic material of [1] or [2], wherein the polymer comprises at least one selected from the group consisting of natural collagen, polyethylene glycol, polyvinyl alcohols and polyglycolic acids.

Item [4] is the hemostatic material of any one of [1] to [3], wherein the nano-fiber is in a form of a nonwoven fabric.

Item [5] is the hemostatic material of [4], wherein a support base material is laminated on the nonwoven fabric.

Item [6] is the hemostatic material of [5], wherein the support base material comprises a polyurethane.

With this invention, the blood coagulation factor is quickly released from the nano-fiber containing the synthetic collagen to the affected part due to the contact with blood, and a high-performance medical material capable of stopping the bleeding in a short time can be provided. Moreover, by incorporating the synthetic collagen into a nano-fiber, the processing toward a hemostatic material is easier and more generally applicable, and the operatability and the productivity of the hemostatic material are improved.

In order to make the aforementioned and other objects, features and advantages of this invention comprehensible, a preferred embodiment accompanied with figures is described in detail below.

DESCRIPTION OF EMBODIMENTS

Figure 1:
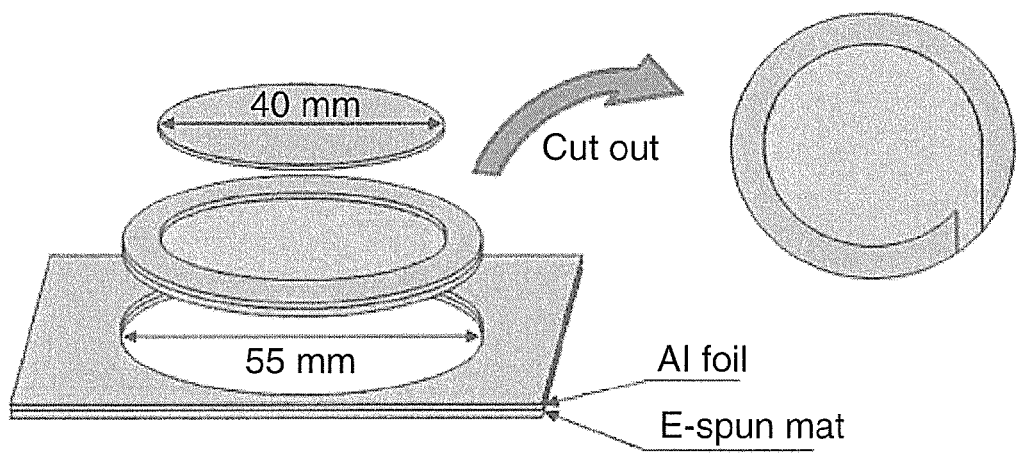
FIG. 1 shows (a) the processing and (b) a photograph of the nonwoven fabric for the bleeding stopping experiments.
Figure 1:
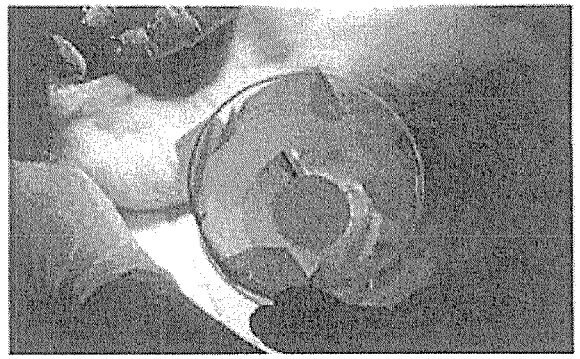

In this invention, the variety of amino acid residues are abbreviated as follows:
Ala: L-alanine residue
Arg: L-arginine residue
Asn: L-asparagine residue
Asp: L-aspartic acid residue
Cys: L-cysteine residue
Gln: L-glutamine residue
Glu: L-glutamic acid residue
Gly: glycine residue
His: L-histidine residue
Hyp: L-hydroxyproline residue
Ile: L-isoleucine residue
Leu: L-leucine residue
Lys: L-lysine residue
Met: L-methionine residue
Phe: L-phenylalanine residue
Pro: L-proline residue
Sar: sarcosine residue
Ser: L-serine residue
Thr: L-threonine residue
Trp: L-tryptophan residue
Tyr: L-tyrosine residue
Val: L-valine residue Moreover, in this specification, the amino acid sequence of the peptide chain is expressed following the general rule, with the N-terminal amino acid residue at the left side and the C-terminal amino acid residue at the right side.

The hemostatic material of this invention includes a nano-fiber that contains a synthetic collagen and a polymer. Though a synthetic collagen is difficult to be included in a nano-fiber in the prior art, the Inventors now have succeeded in spinning a synthetic collagen through electrospinning by using a polymer as a spinning base material.

The method to obtain a nano-fiber containing a synthetic collagen and a polymer is described in details as follows.

<1> Synthetic Collagen

The synthetic collagen in the nano-fiber of this invention is a polypeptide having a peptide fragment represented by formula (1) below (called "poly-PYG", hereinafter), and is sometimes called "synthetic collagen" hereinafter in this specification:

$$-(\text{Pro-Y-Gly})_n- \tag{1}$$

wherein Y is hydroxyproline or praline, wherein the hydroxyproline is, e.g., 4Hyp, and is preferably trans-4-hydroxy-L-proline.

Moreover, in formula (1), the repetition number n is an integer ranging from 5 to 9000. When n is within the range, the polypeptide easily forms into a triple helix structure, and a nano-fiber is easy formed. Moreover, in consideration of the stability of the triple helix structure, n is preferably an integer ranging from 5 to 1000, and more preferably an integer ranging from 10 to 500.

The polypeptide chain of the synthetic collagen in the nano-fiber of this invention may be linear or may have one or more branches. In a case of having a branch, it is possible that the triple helix structure is formed after the branched point, or the branch is present after the triple helix structure.

Moreover, whether the polypeptide has a triple helix structure or not can be confirmed by measuring the circular dichroism spectrum of the polypeptide solution. Specifically, when a positive Cotton effect is shown at 220 to 230 nm and a negative Cotton effect is shown at 195 to 205 nm, the polypeptide is considered to have a triple helix structure.

Moreover, the polypeptide chains of the synthetic collagen in the nano-fiber of this invention may also be crosslinked with each other.

The weight average molecular weight of the synthetic collagen in the nano-fiber of this invention is not particularly limited, and is preferably from 5,700,000 to 7,000,000 and more preferably from 2850 to 300,000 in consideration of the preparation of the spinning solution, the spinning efficiency and stability of the triple helix structure.

Herein, the weight average molecular weight of the synthetic collagen is measured with, e.g., one of the following two methods described in Japan Patent Publication No. 2003-321500. The first method utilizes gel permeation chromatography (GPC) that uses a column of Superdex 200HR 10/30 (made by Ge Helthcare Japan), an eluent of a 10 mM phosphate buffer solution (pH=7.4) containing 150 mM of NaCl at a flow rate of 0.5 ml/min, and Gel Filtration LMW Calibration Kit and Gel Filtration HMW Calibration Kit (made by Ge Helthcare Japan) as molecular weight standards. The second method utilizes GPC that uses a column of Superdex peptide PE 7.5/300 (made by Ge Helthcare Japan), an eluent of a 10 mM phosphate buffer solution (pH=7.4) containing 150 mM of NaCl in a flow rate of 0.25 ml/min, Gel Filtration LMW Calibration Kit (made by Ge Helthcare Japan) and human insulin as molecular weight standards, and glycine. Another method utilizes a HPLC GPC that uses a column of TSK-GEL6000PW XL-CP 8.0×300 mm (made by Tosoh Corporation) at a temperature of 40° C., a mobile phase of 20 mM $KH_2PO_4.H_3PO_4$ (pH=3.0):MeOH=8:2 at a flow rate of 0.5 ml/min, a UV monitor at 215 nm and a differential refractometer for detection, and, as molecular weight standards, pullulan (produced by Showa Denko K.K.) having a molecular weight of 50,000 to 1,600,000 and dextran (produced by Polymer Standards Service GmbH) having a molecular weight of 11,900,000. Moreover, when DAWN HELEOS or Optolab rEX of Wyatt Technology Corporation is used as the detector of the HPLC GPC, the gel permeation chromatograph/multi-angle laser scattering (GPC-MALS) detection method can be used for the measurement. The weight average molecular weights of the synthetic collagen mentioned in this specification are values measured with the above methods.

Although the polypeptide of the synthetic collagen in the nano-fiber of this invention may consist of poly-PYG only, it may also include amino acid residues or a peptide fragment other than poly-PYG, or alkylene, as long as the stability of the triple helix structure is not lowered and the effect desired by this invention is not decreased.

The amino acid residue contained may be at least one selected from Ala, Arg, Asn, Asp, Cys, Gln, Glu, Gly, His, Hyp, Ile, Leu, Lys, Met, Phe, Pro, Sar, Ser, Thr, Trp, Tyr and Val. The peptide fragment may be a peptide formed by bonding a plurality of one or more kinds of those amino acid residues. The alkylene may be straight or branched, and is not particularly limited. However, the alkylene is specifically exemplified by $C_{1-18}$ alkylene, and is preferably $C_{2-12}$ alkylene in practice.

In the polypeptide of the synthetic collagen in the nano-fiber of this invention, the weight ratio of poly-PYG to the amino acid residues or the peptide fragment other than poly-PYG or alkylene ranges from 1:99 to 100:0, and preferably ranges from 10:90 to 100:0.

The polypeptide of the synthetic collagen in the nano-fiber of this invention may also forms a salt with an inorganic acid (hydrochloric acid or sulfuric acid, etc.), an organic acid (acetic acid, lactic acid, maleic acid, oxalic acid or citric acid, etc.), a metal (sodium or potassium, etc.), or an organic base (trimethylamine or triethylamine, etc.). The salt compounds of the polypeptide of the synthetic collagen in the nano-fiber of this invention may be used alone or in combination of two or more.

The polypeptide including poly-PYG may be obtained with an arbitrary method.

For example, by conducting a condensation reaction of a peptide oligomer formed from the amino acids constituting the poly-PYG by a known solid-state or liquid-state synthesis method, the polypeptide can be obtained in a preferred manner.

The condensation reaction of the above peptide oligomer is usually conducted in a solvent. Any solvent can be used as long as it is able to dissolve (partially or fully) or disperse the peptide oligomer as the raw material, and water or an organic solvent can be used usually. Specific examples of the solvent include water, amides (dimethylformamide, dimethylacetoamide and hexamethylphosphoramide, etc.), sulfoxides (dimethylsulfoxide, etc.), nitrogen-containing cyclic compounds (N-methylpyrrolidone and pyridine, etc.), nitriles (acetonitrile), ethers (dioxane and tetrahydrofuran, etc.), alcohols (methanol, ethanol and propanol, etc.), mixed solvents thereof and so on. Among them, water, dimethylformamide and dimethylsulfoxide are preferably used.

Moreover, the condensation reaction of the above peptide oligomer is preferably conducted in the presence of a dehydrating agent (a dehydration condensation agent or a condensation assistant). When the reaction is conducted in the presence of a dehydration condensation agent or a condensation assistant, a complicated treatment of repeating deprotection and amino-acid bonding is not required, and dimerization or cyclization is inhibited. Thereby, the condensation reaction is able to run smoothly.

The dehydration condensation agent is not particularly limited as long as it can efficiently cause dehydration condensation in the above solvent. Examples thereof include carbodiimide-series condensation agents, such as diisopropylcarbodiimide (DIPC), 1-ethyl-3-(3-dimethylaminopropyl)carbodiimide (EDC=WSCI), hydrochloric salt of 1-ethyl-3-(3-dimethylaminopropyl)carbodiimide (WSCI.HCl) and dicyclohexylcarbodiimide (DCC), etc.; fluorophosphates-series condensation agents, such as O-(7-azabenzotriazol-1-yl)-1,1,3,3-tetramethyluronium hexafluorophosphate, O-benzotriazol-1-yl-N,N,N',N'-tetramethyluronium hexafluorophosphate, benzotriazole-1-yl-oxy-tris-pyrrolidinophosphonium hexafluorophosphate, and benzotriazole-1-yl-tris(dimethylamino)phosphonium hexafluorophosphide salt (BOP), etc.; and diphenylphosphoryl azide (DPPA).

These dehydration condensation agents can be used alone or in combination of two or more. The preferred agents among them are the carbodiimide-series condensation agents, such as 1-ethyl-3-(3-dimethylaminopropyl)carbodiimide, and the hydrochloric salt of 1-ethyl-3-(3-dimethylaminopropyl)carbodiimide.

When a non-aqueous solvent not containing water is used, the amount of the dehydration condensation agent used per mole of the total amount of the peptide fragment is usually 0.7 to 5 moles, preferably 0.8 to 2.5 moles and more preferably 0.9 to 2.3 moles (e.g., 1 to 2 moles). When a solvent containing water, i.e., an aqueous solvent, is used, water deactivates the dehydration condensation agent, and the amount of the dehydration condensation agent used per mole of the total amount of the peptide fragment is usually 2 to 500 moles, preferably 5 to 250 moles and more preferably 10 to 125 moles.

The condensation assistant is not particularly limited as long as it can promote the condensation reaction. Examples thereof include N-hydroxypolycarboxylic imides, such as N-hydroxydicarboxylic imides including N-hydroxysuccinimide (HONSu) and N-hydroxy-5-norbonene-2,3-dicarboxylic imide (HONB), etc.; N-hydroxytriazoles, such as N-hydroxybenzotriazoles including 1-hydroxybenzotriazole (HOBt), etc.; triazines, such as 3-hydroxy-4-oxy-3,4-dihydro-1,2,3-benzotriazine (HOOBt); and ethyl ester of 2-hydroxyimino-2-cyanoacetic acid.

These condensation assistants can be used alone or in combination of two or more. The preferred ones among them are N-hydroxydicarboxylic imides (such as HONSu), N-hydroxybenzotriazoles (such as HOOBt) and N-hydroxybenzotriazines.

The amount of the condensation assistant used is regardless of the species of the solvent, and is usually 0.5 to 5 moles, preferably 0.7 to 2 moles and more preferably 0.8 to 1.5 mole, relative to one mole of the total amount of the peptide fragment.

It is preferred to use a combination of a dehydration condensation agent and a condensation assistant. Examples of such combination include DCC-HONSu (HOBt or HOOBt) and WSCI-HONSu (HOBt or HOOBt).

In the condensation reaction of the above peptide oligomer, the pH value of the reaction solution may be adjusted, usually to be around a neutral state (pH is about 6 to 8). The pH adjustment can be carried out usually with an inorganic base (NaOH, KOH, sodium carbonate or sodium hydrogencarbonate, etc.), an organic base, an inorganic acid (such as hydrochloric acid), or an organic acid.

Moreover, a base not participating in the condensation reaction may also be added in the reaction solution. Examples of such base include: tertiary amines, such as trialkylamines including trimethylamine, triethylamine and diisopropylethylamine, etc.; and heterocyclic tertiary amines, such as N-methylmorpholine and pyridine, etc. The amount of such base used is usually about one to two times of the total molar number of the peptide oligomer.

In the polypeptide obtained as above, there are residues of the reagents used in the reactions. Because the residues will affect the spinning process of the nano-fiber, they are preferably removed. Removal of the residual reagents may utilize a known method, such as a dialysis method, a column method or an ultra-filtration method.

Moreover, in consideration of the stability and easy operation of the polypeptide, it is preferred to substitute the reaction solvent with a preservation solvent. When a dialysis method is used, substitution of the reaction solvent with the target preservation solvent is carried out by using the target preservation solvent as a dialysis outer liquid. When a column method is used, the substitution is carried out by using the target preservation solvent as a mobile phase.

The preservation solvent is not particularly limited, as long as it is able to inhibit the change of the physical properties and so on of the polypeptide obtained as the effective component. Examples thereof include water, saline, and a buffer liquid with a buffering effect from weak acid to weak alkali. However, it is preferred that the preservation solvent does not contain any substance that affects the spinning process of the nano-fiber.

<2> Polymer

The polymer contained in the nano-fiber being the raw material of the hemostatic material of this invention serves as the spinning base material in the spinning of the nano-fiber. By using the polymer as the spinning base material, the synthetic collagen, which is conventionally difficult to include in a nano-fiber, is possible to spin with an electrospinning method. As a result, uniform and long-fibrous nano-fibers containing the synthetic collagen can be obtained, and the processing of the hemostatic material is easier.

The polymer in the nano-fiber of this invention is not particularly limited, as long as it is biocompatible and can be used as a spinning base material. For example, the polymer preferably includes one, two or more species selected from polyethylene glycol, polyvinyl alcohol, polyglycolic acid and natural collagen, etc.

The weight average molecular weight of the polymer used in this invention is not particularly limited, and is preferably from 50,000 to 1,000,000 and more preferably from 60,000 to 900,000. Moreover, said weight average molecular weight can be measured using a GPC method or a light scattering method.

<3> Solvent

When the nano-fiber of this invention is being spun, the synthetic collagen and the polymer are dissolved in a solvent.

The solvent is not particularly limited, as long as it can dissolve the synthetic collagen and the polymer and can be evaporated in the spinning step to allow formation of a fiber. Examples of the solvent include water, ethanol, methanol, isopropanol, acetone, sulfolane-acetone, propanol, dichloromethane, formic acid, hexafluoroisopropanol, hexafluoroacetone, methyl ethyl ketone, chloroform, toluene, tetrahydrofuran, benzene, benzyl alcohol, 1,4-dioxane, carbon tetrachloride, cyclohexane, cyclohexanone, methylene dichloride, phenol, pyridine, trichloroethane, acetic acid, N,N-dimethylformamide, dimethylsulfoxide, N,N-dimethylacetoamide, 1-methyl-2-pyrrolidone, ethylene carbonate, propylene carbonate, dimethyl carbonate, acetonitrile, N-methylmorpholine-N-oxide, butylene carbonate, 1,4-butyrolactone, diethyl carbonate, diethyl ether, 1,2-dimethoxyethane, 1,3-dimethyl-2-imidazolidinone, 1,3-dioxolane, ethyl methyl carbonate, methyl formate, 3-methyloxazolidine-2-one, methyl propionate, and 2-methyltetrahydrofuran, etc. These solvents may be used alone or in combination of two or more.

<4> Other Components

The spinning solution prepared for producing the nano-fiber of this invention may also contain arbitrary component other than the above essential components in a manner such that the spinning is not hindered. Examples of the arbitrary component include an adhesive agent and an electrolyte.

By adding an adhesive agent, the produced nano-fibers are bonded to each other at their contact points, so that when the nano-fiber is obtained in the form of a nonwoven fabric, a soft nonwoven fabric with few fluffs can be obtained due to the strong friction. The adhesive agent is not particularly limited as long as it is able to bond the produced nano-fibers and can be dissolved in the solvent of the spinning solution. Examples of the adhesive agent include adhesive agents formed from hot melt resins, elastomer-type adhesive agents, acryl-type adhesive agents, epoxy-type adhesive agents, vinyl-type adhesive agents, and so on. Examples of the elastomer-type adhesive agents include polychloroprene rubber, styrene-butadiene rubber, butyl rubber, acrylonitrile-butadiene rubber, ethylene-propylene rubber, chlorosulfonated polyethylene rubber and epichlorohydrin rubber. In a case where an adhesive agent is to be added, the addition amount relative to the total weight of the synthetic collagen and the polymer contained in the spinning solution preferably ranges from 0.5 wt % to 10 wt %.

On the other hand, by adding an electrolyte, the charge density on the surface of the spinning solution can be raised, so that the spinnability is possible to improve. The electrolyte is not particularly limited, as long as it is dissolvable in the spinning solution and can be electrolytically dissociated in the same. Examples thereof include sodium chloride, calcium chloride, magnesium chloride, sodium carbonate, sodium hydrogen-carbonate, and magnesium carbonate. In a case where an electrolyte is added, it is desired that the addition amount does not cause salting-out of the synthetic collagen and the polymer in the spinning solution. The addition amount preferably ranges from 0.5 wt % to 10 wt %, relative to the total amount of the synthetic collagen and the polymer in the spinning solution.

<5> Method for Producing Nano-Fiber

The nano-fiber of this invention can be produced with steps comprising: a step of dissolving a synthetic collagen and a polymer in a solvent to prepare a spinning solution, and a step of spinning fibers through electrospinning using the spinning solution.

The spinning solution may be prepared by dissolving the synthetic collagen and the polymer in respective solvents and then mixing the respective solutions, or by dissolving arbitrary one of the synthetic collagen and the polymer in a solvent and then adding and dissolving the other of the same in the resulting solution. Moreover, during the preparation, heating and stirring can be conducted properly, as long as the synthetic collagen is not degenerated by the heating or stirring.

The concentration of the synthetic collagen in the spinning solution is preferably from 0.1 wt % to 2.0 wt % and more preferably from 0.5 wt % to 1.0 wt %. Moreover, the concentration of the polymer in the spinning solution is preferably from 0.1 wt % to 20 wt % and more preferably from 0.5 wt % to 10 wt %. By setting the concentrations of the synthetic collagen and the polymer in the respective ranges, interactions between the polymer chains and between the polymer and the synthetic collagen are generated in the spinning solution, and contiguous fibers are easy to form.

In order to obtain uniform nano-fibers with a certain length, the combination ratio of the synthetic collagen to the polymer in the spinning solution is preferably from 20:1 to 1:100 by weight and more preferably 10:1 to 1:40 by weight.

The spinning step is conducted through electrospinning (electric-field spinning) using the above spinning solution.

Thereby, nano-scale fibers with small and uniform diameters can be produced, so that a fibrous material with a large specific surface area is obtained, and the nano-fibers are easily obtained as a nonwoven fabric. Therefore, the nano-fiber is suitably used as a raw material of a hemostatic material that has a high performance and a good operatability.

The electrospinning can be conducted with a well known operation. Specifically, a voltage is applied between a nozzle filled with the spinning solution and a collector (substrate), the spinning solution is discharged from the nozzle, and fibers are collected on the collector. The conditions of the electrospinning are not particularly limited, and may be properly adjusted according to the type of the spinning solution, the use of the obtained nano-fiber, and so on. The general conditions in the method of this invention include, for example, a voltage of 8 to 30 kV, a discharge rate of 0.01 to 1.00 mL/hour, a vertical distance of 100 to 200 mm between the nozzle and the collector, and a nozzle diameter of 22 to 25 G. The spinning atmosphere preferably has a relative humidity of 10% to 40% and a temperature of 10° C. to 25° C., but may be set without precise control.

With the above production method, fibers having a diameter of 5 nm to 50 μm can be obtained. Moreover, by setting/adjusting the spinning conditions, contiguous nano-fibers with an average length of 200 to 300 nm can be obtained. Meanwhile, block-shaped beads are not or rarely contained in the nano-fibers, and therefore uniform nano-fibers can be obtained.

Moreover, in consideration of assuring the hemostatic performance, the content of the synthetic collagen in the nano-fiber is preferably from 1 wt % to 90 wt % and more preferably from 2.5 wt % to 90 wt %. Said content can be adjusted arbitrarily in the aforementioned preparation process of the spinning solution.

By using the nano-fiber obtained in the above manner, the hemostatic material of this invention can be formed. The hemostatic material of this invention may have a sufficient hemostatic performance without additionally containing a blood coagulation factor such as thrombin, or may contain a blood coagulation agent or an additive, etc., if required, and is not particularly limited in this aspect. For example, a hemostatic component such as thrombin, fibrinogen or oxidized cellulose, a cell adhesion protein such as fibronectin, vitronectin or laminin, or aprotinin, aminocaproic acid or tranexamic acid showing an antifibrolytic effect, can also be contained in the hemostatic material of this invention. Moreover, various additives, such as a stabilizer (such as an amino acid species like albumin or hydrochloric salt of arginine), an antibacterial agent, a preservative, or other vitamin species or physiologically allowable salt, etc., may also be contained in the hemostatic material of this invention.

Moreover, in consideration of good operability and processability, the nano-fiber in the hemostatic material of this invention is preferably in the form of a nonwoven fabric. In consideration of the operability, the thickness of the nonwoven fabric is preferably from 0.01 mm to 0.5 mm and more preferably from 0.1 mm to 0.3 mm.

Moreover, for a hemostatic material in a nonwoven fabric form, it is preferred to laminate a support base material thereon in consideration of improving the hemostatic performance. The form of the support base material is not particularly limited to a film, a nonwoven fabric, a gel or a plate, etc., and the material of the same is either not particularly limited. For example, a polymer like polyurethane is a preferred material in consideration of the operability. Said support base material layer can be formed with any possible method, for example, a method of laminating/affixing a polyurethane film on a single surface of the nonwoven fabric. Moreover, in consideration of the operatability and the hemostatic performance, the thickness of the support base material is preferably from 0.01 mm to 0.3 mm and more preferably from 0.1 mm to 0.2 mm.

Moreover, for the hemostatic material of this invention, thought the nano-fiber or its nonwoven fabric may be directly provided for hemostatic, the operatability can be further improved by processing the nano-fiber or its nonwoven fabric into a shape disposed on a suitable support. For example, as illustrated in FIG. 1, by applying the collector substrate used during the spinning as a support, the hemostatic material can have a size or a shape fitting the affected part.

When the hemostatic material of this invention is used to stop bleeding, it is used in contact with the affected part requiring the bleeding to stop, such as an abrasion or cut wound. In such a case, the hemostatic material may be pressed on the affected part while in contact with the same, or may not be pressed on the same. By contacting the hemostatic material with the blood, the synthetic collagen as a blood coagulation factor is quickly released from the nano-fibers with a large specific surface area contained in the hemostatic material, and the bleeding can be stopped in a short period of time in the scale of several seconds to tens of seconds.

EXAMPLES

This invention will be further explained in details by the following examples, but the scope of this invention is not limited by the examples.

<<Production of Nonwoven Fabric of Nano-Fiber>>

The nano-fiber nonwoven fabrics of Examples 1 to 3 and Comparative Examples 1 and 2 were produced through electrospinning.

Example 1

Nonwoven Fabric of SC/PEG Blend Nano-Fibers

A 0.5 wt % aqueous solution of a synthetic collagen (SC, produced by JNC Corporation) and a 10 wt % aqueous solution of polyethylene glycol (PEG, with a weight average molecular weight of 500,000, produced by Wako Pure Chemical Industries, Ltd.) were prepared respectively, and were mixed in a volume ratio of SC:PEG=2:1 to obtain a spinning solution. A voltage of 8 kV was applied, by a high-voltage generation apparatus, between a 25 G stainless needle and a collector made of an Al foil with a vertical distance of 200 mm. The spinning solution was filled in a syringe connected with the above needle and was extruded onto the collector in a discharge rate of 0.01 mL/hour, and a uniformly distributed nonwoven fabric was collected. Moreover, the humidity of the spinning atmosphere was controlled by introducing a dry nitrogen gas, and was maintained constantly at a relative humidity of 15% or less in the spinning. Furthermore, the temperature of the spinning atmosphere was not controlled, and the spinning was conducted at room temperature.

The content of the synthetic collagen in the above spun SC/PEG blend nano-fibers was 9.1 wt %. The Al foil as the spinning collector was processed into the shape of a support frame of the nonwoven fabric, as shown in FIG. 1.

Example 2

Laminated Nonwoven Fabric of SC/PEG Blend Nano-Fibers and Polyurethane Film

Figure 2:
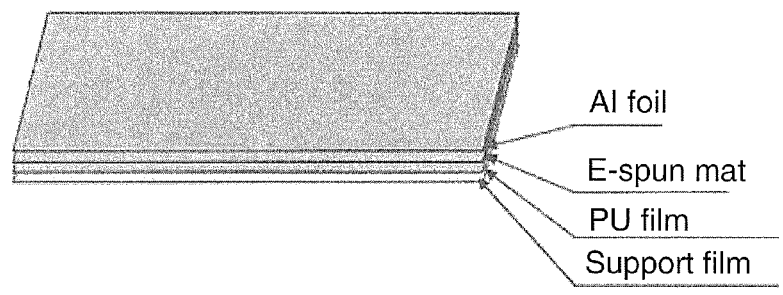
FIG. 2 shows (a) an illustration and (b) some photographs of a nonwoven fabric laminated with a polyurethane film.
Figure 2:
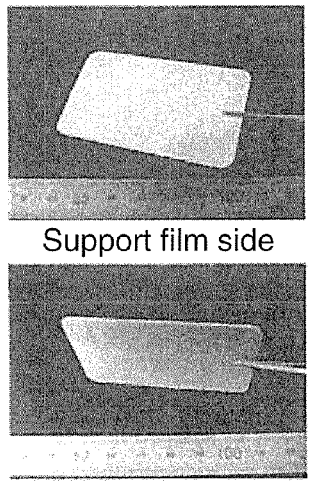

A SC/PEG blend nano-fiber nonwoven fabric was produced with the same operations of Example 1, and a polyurethane film was affixed on the surface of the nonwoven fabric to form a nonwoven fabric laminated with a polyurethane film, as shown in FIG. 2.

Example 3

Nonwoven Fabric of SC/PVA Blend Nano-Fibers

A 0.5 wt % aqueous solution of a synthetic collagen (SC, produced by JNC Corporation) and a 20 wt % aqueous solution of polyvinyl alcohol (PVA, with a mean polymerization degree of 1,500 and a saponification degree of 78 to 82 mol %, produced by Wako Pure Chemical Industries, Ltd.) were prepared respectively, and were mixed in a volume ratio of SC:PVA=1:1 to obtain a spinning solution. A voltage of 12 kV was applied, by a high-voltage generation apparatus, between a 25 G stainless needle and a collector made of an Al foil with a vertical distance of 180 mm. The spinning solution was filled in a syringe connected with the above needle and was extruded onto the collector in a discharge rate of 0.08 mL/hour, and a uniformly distributed nonwoven fabric was collected. Moreover, the humidity of the spinning atmosphere was controlled by introducing a dry nitrogen gas, and was maintained constantly at a relative humidity of 15% or less in the spinning. Furthermore, the temperature of the spinning atmosphere was not controlled, and the spinning was conducted at room temperature.

The content of the synthetic collagen in the above spun SC/PVA blend nano-fibers was 2.4 wt %. The Al foil as the spinning collector was processed into the shape of a support frame of the nonwoven fabric, as shown in FIG. 1.

Comparative Example 1

Nonwoven Fabric of NC Nano-Fibers

A natural collagen (NC; NMP Collagen PS/IP, produced by Nippon Meat Packers, Inc.) was dissolved in 1,1,1,3,3,3-hexafluoro-2-propanol (HFIP, produced by Wako Pure Chemical Industries, Ltd.) in a concentration of 100 mg/mL to form a spinning solution. A voltage of 14 kV was applied, by a high-voltage generation apparatus, between a 25 G stainless needle and a collector made of an Al foil with a vertical distance of 100 mm. The spinning solution was filled in a syringe connected with the above needle and was extruded onto the collector in a discharge rate of 0.06 mL/h, and a uniformly distributed nonwoven fabric was collected. Moreover, the humidity of the spinning atmosphere was controlled by introducing a dry nitrogen gas, and was maintained constantly at a relative humidity of 15% or less in the spinning. Furthermore, the temperature of the spinning atmosphere was not controlled, and the spinning was conducted at room temperature.

In the above spun nonwoven fabric of NC nano-fibers, the Al foil as the spinning collector was also processed into the shape of a support frame of the nonwoven fabric, as shown in FIG. 1.

Comparative Example 2

Nonwoven Fabric of PVA Nano-Fibers

A 20 wt % aqueous solution of polyvinyl alcohol (PVA with a mean polymerization degree of 1,500 and a saponification degree of 78 to 82 mol %, produced by Wako Pure Chemical Industries, Ltd.) was prepared as a spinning solution. A voltage of 12 kV was applied, via a high-voltage generation apparatus, between a 25 G stainless needle and a collector made of an Al foil with a vertical distance of 180 mm. The spinning solution was filled in a syringe connected with the above needle and was extruded onto the collector in a discharge rate of 0.04 mL/h, and a uniformly distributed nonwoven fabric was collected. Moreover, the humidity of the spinning atmosphere was controlled by introducing a dry nitrogen gas, and was maintained constantly at a relative humidity of 15% or less in the spinning. Furthermore, the temperature of the spinning atmosphere was not controlled, and the spinning was conducted at room temperature.

In the above spun nonwoven fabric of PVA nano-fibers, the Al foil as the spinning collector was also processed into the shape of a support frame of the nonwoven fabric, as shown in FIG. 1.

<<Bleeding-Stopping Experiment>>

The nano-fiber nonwoven fabric produced as above was used as a sample to observe the hemostatic performance. The experiment procedure is described as follow.

An abrasion wound of about 10 mm$^2$ was made, by using a surgical knife, on the surface of the liver of a white rabbit to cause bleeding, and the bleeding was confirmed to continue when no treatment was administered. The entire abrasion wound was covered by affixing the sample thereto. No pressing or the like was applied from the top of the sample.

Moreover, a cut wound of about 15 mm was induced, by using a surgical knife, on the surface of the liver of a white rabbit to cause bleeding, and the bleeding was confirmed to continue when no treatment was administered. The entire cut wound was covered by affixing the sample thereto. No pressing or the like was applied from the top of the sample.

With respect to the nano-fiber nonwoven fabric of Examples 1-3 and Comparative Examples 1-2, the experiment results are described as follows.

Test Example 1

Nonwoven Fabric of SC/PEG Blend Nano-Fibers

Figure 3:
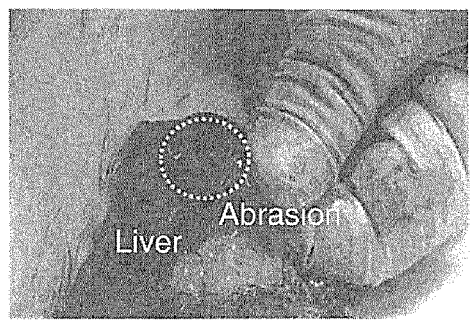
FIGS. 3(a)-(d) are photographs showing a bleeding stopping experiment (abrasion) using the sample of Example 1.
Figure 3:
Figure 3:
Figure 3:

After the abrasion wound was made, the bleeding went on when no treatment was administered (FIG. 3a). However, after the sample produced in Example 1 was affixed to the wound (FIG. 3b), the portion of the sample in contact with the blood was dissolved simultaneously with the contact, and the sample quickly adhered tightly to the surface of the liver (FIG. 3c). After the sample was affixed on the abrasion wound, the blood leaking to the outside of the liver stopped at least within 30 seconds (FIG. 3d). According to visual observation, the sample did not maintain the form of a nonwoven fabric, but formed a thin gel-like film on the surface of the abrasion wound (FIG. 3d). The bleeding continued under the gel-like layer was observed, and the leaking of a small amount of blood from the gel-like layer was confirmed.

Figure 4:
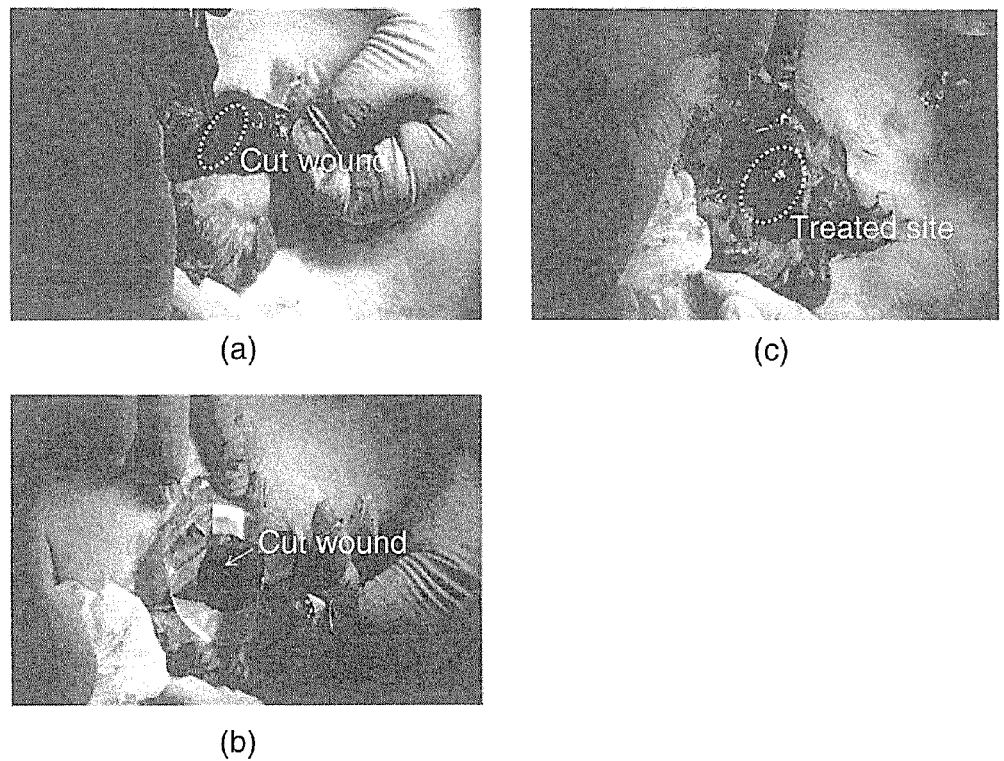
FIGS. 4(a)-(c) are photographs showing another bleeding stopping experiment (cut wound) using the sample of Example 1.

On the other hand, after the cut wound was induced, the bleeding continued when no treatment was administered (FIG. 4a). However, after the sample was affixed to the wound (FIG. 4b), the portion of the sample in contact with the blood was dissolved simultaneously with the contact, and the sample quickly adhered tightly to the surface of the liver to foil n a thin gel-like layer (FIG. 4c). Because the amount of the synthetic collagen in the affixed sample is insufficient relative to the blood amount, a complete stop of the bleeding was not achieved, and a small amount of the blood leaked from the crack of the gel-like layer together with the beating. However, the blood in contact with the sample quickly coagulated and a thin gel-like layer was formed, and it was confirmed that further blood leaking from the gel-like layer was prevented. The blood coagulation reaction caused by the contact of the sample and the blood occurred almost simultaneously with formation of the gel-like layer, and it was supposed that the time required by the reaction was approximately within several seconds.

Test Example 2

Laminated Nonwoven Fabric of SC/PEG Blend Nano-Fibers and Polyurethane Film

Figure 5:
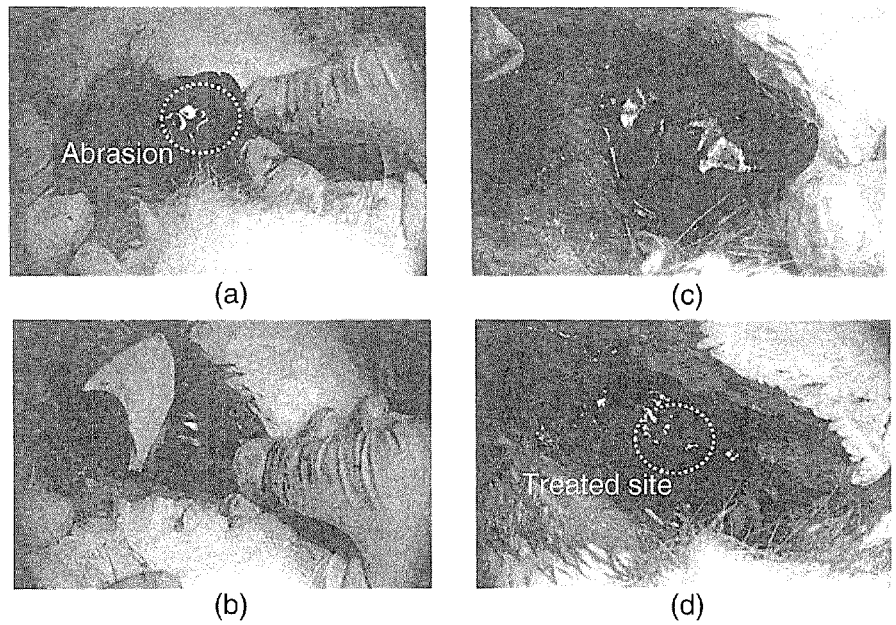
FIGS. 5(a)-(d) are photographs showing a bleeding stopping experiment (abrasion) using the sample of Example 2.

After the abrasion wound was induced, the bleeding continued when no treatment was administered (FIG. 5a). After the sample produced in Example 2, from which the Al foil was peeled off to expose the surface of the nonwoven fabric, was affixed to the wound, the support film was removed (FIG. 5b). The portion of the sample in contact with the blood was dissolved simultaneously with the contact, and the sample quickly adhered tightly to the surface of the liver (FIG. 5c). After the sample was affixed on the abrasion wound, the blood leaking to the outside of the liver stopped at least within 30 seconds (FIG. 5d). After the sample had been affixed for one minute, no bleeding pattern was observed. Moreover, the bleeding site could be observed through the polyurethane film at the same time. After the sample had been affixed for 3 minutes, the polyurethane film was peeled off from the abrasion wound, and a gel-like layer was confirmed to form on the surface of the liver. After the polyurethane film was removed, a small amount of bleeding was observed.

Figure 6:
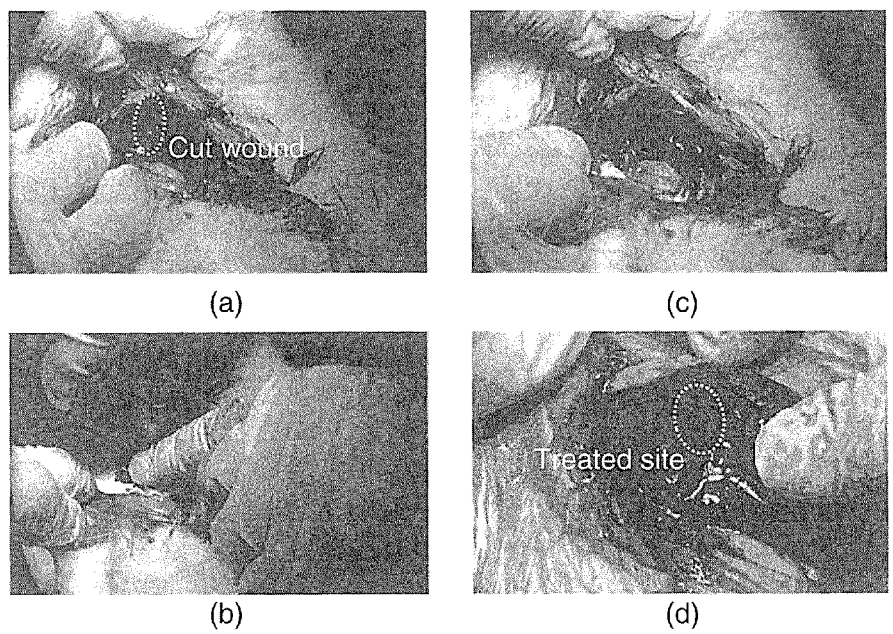
FIGS. 6(a)-(d) are photographs showing another bleeding stopping experiment (cut wound) using the sample of Example 2.

On the other hand, after the cut wound was induced, the bleeding continued when no treatment was administered (FIG. 6a). After the sample was affixed to the wound and after the Al foil was peeled off to expose a surface of the nonwoven fabric (FIG. 6b), the support film was removed (FIG. 6c). The portion of the sample in contact with the blood was dissolved at the same time of the contact, and the sample quickly adhered tightly to the surface of the liver (FIG. 6c). After the sample had been affixed for one minute, no bleeding pattern was observed. The bleeding site could be observed through the polyurethane film. After the sample had been affixed for 5 minutes, stopping of the bleeding was confirmed, the polyurethane film was peeled from the affected part, and formation of a gel-like layer on the surface of the liver was confirmed (FIG. 6d). After the polyurethane film was removed, no bleeding was observed.

Test Example 3

Nonwoven Fabric of SC/PVA Blend Nano-Fibers

Figure 7:
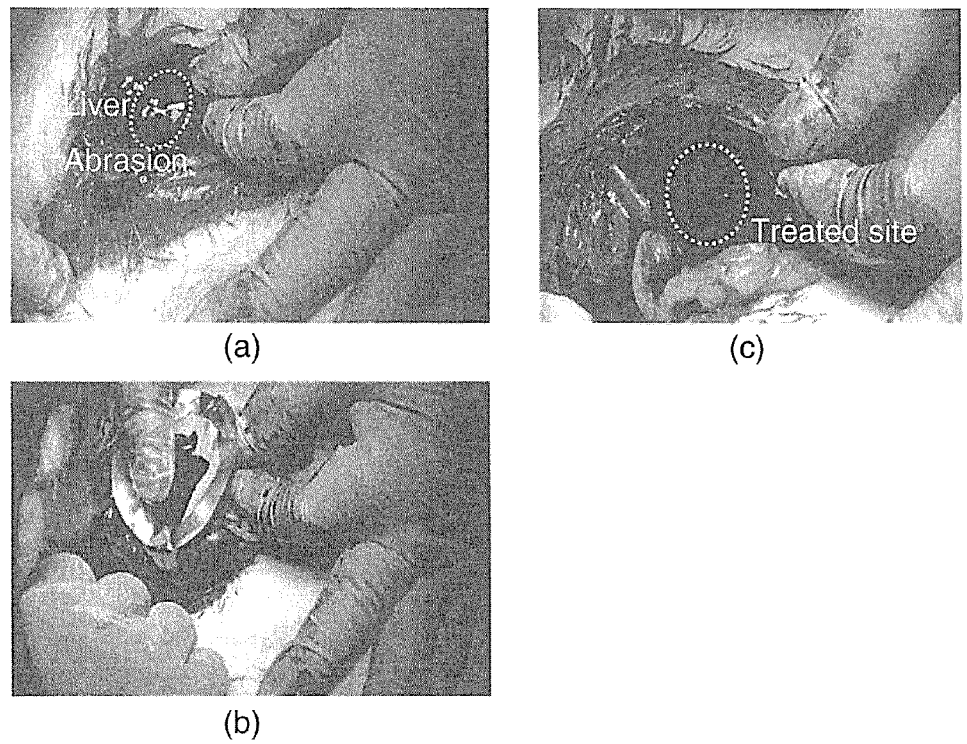
FIGS. 7(a)-(c) are photographs showing a bleeding stopping experiment (abrasion) using the sample of Example 3.

After the abrasion wound was induced, the bleeding continued when no treatment was administered (FIG. 7a). After the sample produced in Example 3 was affixed to the wound (FIG. 7b), the portion of the sample in contact with the blood was dissolved at the same time of the contact, and the sample quickly adhered tightly to the surface of the liver. After the sample was affixed on the abrasion wound, the blood leaking to the outside of the liver stopped at least within 60 seconds (FIG. 7c). According to visual observation, the sample did not maintain the form of a nonwoven fabric but formed a thin gel-like film on the surface of the abrasion wound (FIG. 7c).

Figure 8:
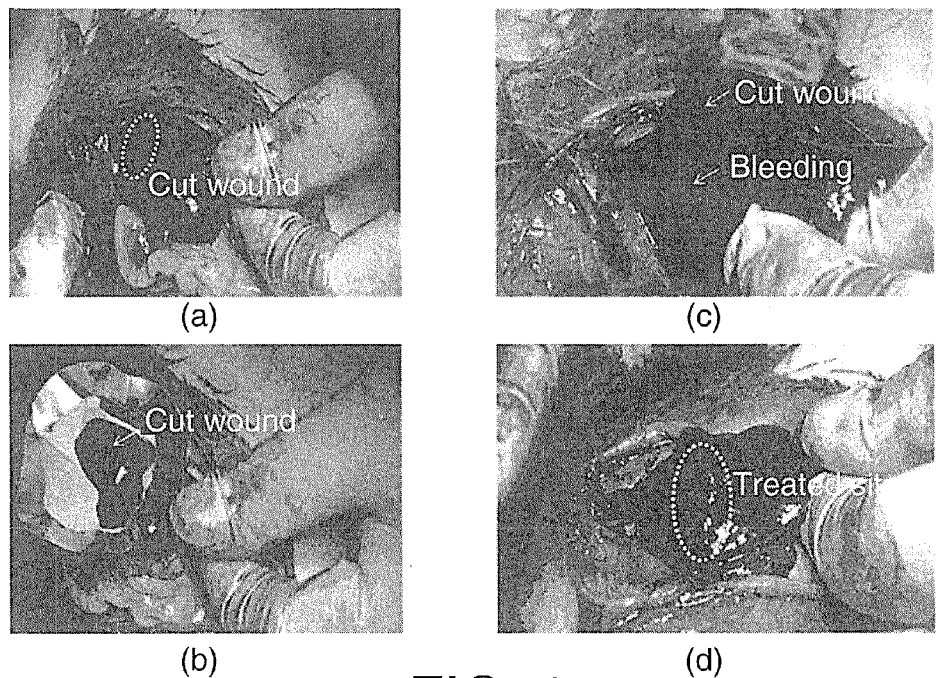
FIGS. 8(a)-(d) are photographs showing another bleeding stopping experiment (cut wound) using the sample of Example 3.

On the other hand, after the cut wound was induced the bleeding continued when no treatment was administered (FIG. 8a). After the sample was affixed to the wound (FIG. 8b), the portion of the sample in contact with the blood was dissolved at the same time of the contact, and the sample quickly adhered tightly to the surface of the liver to form a thin gel-like layer. However, because the amount of the synthetic collagen in the affixed sample is insufficient relative to the blood amount, a complete stop of the bleeding was not achieved, and a small amount of the blood leaked from the crack of the gel-like layer together with the beating (FIG. 8c). A new cut wound with less blood leaking was induced at another site of the surface of the liver for a further bleeding stopping experiment, and a quick hemostatic effect together with a formation of a gel-like layer was confirmed.

Comparative Test Example 1

Nonwoven Fabric of NC Nano-Fibers

Figure 9:
FIGS. 9(a)-(c) are photographs showing a bleeding stopping experiment (cut wound) using the sample of Comparative Example 1.
Figure 9:
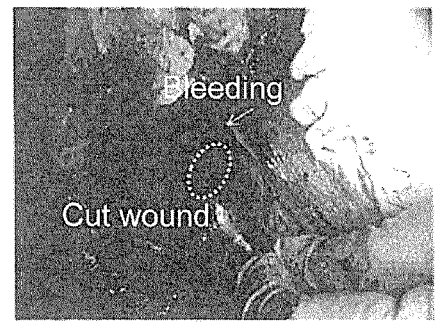
Figure 9:

After a cut wound was made, the bleeding continued when no treatment was administered (FIG. 9a). After the Al foil was peeled off, the sample produced in Comparative Example 1 was affixed to cover the entire cut wound (FIG. 9b). The nonwoven fabric directly absorb water after contacting with the blood and softened to adhere tightly to the surface of the liver; however, no blood coagulation pattern was identified, and the bleeding continued after the sample was affixed to the wound (FIG. 9c).

Comparative Test Example 2

Nonwoven Fabric of PVA Nano-Fibers

Figure 10:
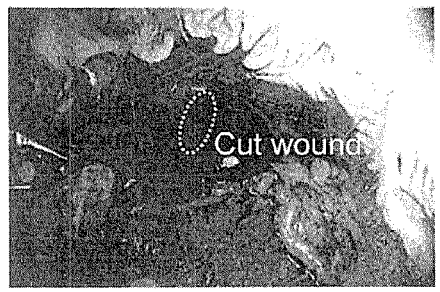
FIGS. 10(a)-(c) are photographs showing a bleeding stopping experiment (cut wound) using the sample of Comparative Example 2.
Figure 10:
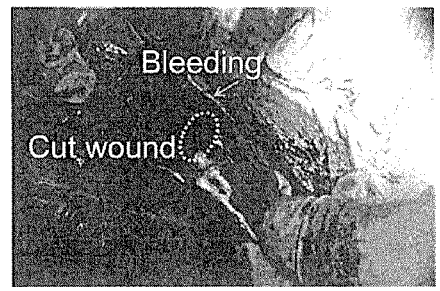
Figure 10:

After a cut wound was induced, the bleeding continued when no treatment was administered (FIG. 10a). After the Al foil was peeled off, the sample produced in Comparative Example 2 was affixed to cover the entire cut wound (FIG. 10b). The nonwoven fabric was directly dissolved after contacting with the blood to adhere tightly to the surface of the liver. However, as being different from the cases of those samples containing the synthetic collagen, no blood coagulation pattern was identified (FIG. 10c) even though a gel-like layer was also formed on the surface of the liver.

<<Blood Coagulation Test>>

The nonwoven fabric of SC/PEG blend nano-fibers of Example 1 and a freeze-dried SC/PEG sponge were used to conduct a blood coagulation test according to the Lee-White method. The freeze-dried SC/PEG sponge was produced by respectively preparing a 0.5 wt % aqueous solution of a synthetic collagen (SC, produced by JNC Corporation) and a 10 wt % aqueous solution of polyethylene glycol (PEG, with a weight average molecular weight of 500,000, produced by Wako Pure Chemical Industries, Ltd.), mixing the solutions in a volume ratio of SC:PEG=2:1, dripped the mixture into a Teflon® container, and freezing the same to −80° C. for freeze-drying.

The procedure of the blood coagulation test is described as follows.

A rabbit was put to sleep by injecting 1.6 mL of an anesthetic to its auricular vein. Its blood of about 20 mL was drawn from the heart to a syringe (with a size of 50 mL, using a 18 G needle) containing 2 mL of a 3.13% aqueous solution of citric acid, so as to obtain citric acid-treated blood.

Glass tubes, each of which was loaded with a sample having the amount shown in Table 1, were prepared. After 1 mL of the citric acid-treated blood was loaded in each glass tube, all the glass tubes were quickly added with a 30 µL aqueous solution of calcium chloride, lightly shake-stirred and dipped in a thermostat of 37° C. The glass tubes of the column "a" were taken out per 15 to 30 seconds and inclined to identify the coagulation pattern. After coagulation was identified in the glass tubes of the column "a", the glass tubes of the column "b" having been placed still were similarly observed for the coagulation pattern.

TABLE 1

|  | a | b |
|---|---|---|
| Nano-fiber nonwoven fabric | 1.0 | 1.2 |
| Freeze-dried sponge | 1.2 | 1.1 |

(unit: mg)
a: glass tubes that were taken out from the thermostat and observed at a fixed interval
b: glass tubes that were placed still in the thermostat until the coagulation in the glass tubes a was identified The measurement result of the coagulation time in each glass tube is shown in Table 2. In each of the sets a and b, the coagulation of the nano-fiber nonwoven fabric is always shorter by about 30 seconds than that of the freeze-dried sponge.

Thus, it is clear that the blood coagulation efficiency was improved by incorporating the synthetic collagen into nano-fibers. The reason is supposed to be that the nano-fibers have large surface areas, and therefore the contact area with blood is also large.

TABLE 2

|  | Blood coagulation time | |
|---|---|---|
|  | a | b |
| Nano-fiber nonwoven fabric | 2 min and 50 sec | 4 min and 15 sec |
| Freeze-dried sponge | 3 min and 20 sec | 4 min and 45 sec |

INDUSTRY UTILITY

Based on this invention, a high-performance medical material capable of stopping bleeding in short time can be provided. Moreover, by using nano-fiberized synthetic collagen as a raw material of a hemostatic material, the processing to the hemostatic material is easy and the applicability is broad, and the operatability and the productivity of the hemostatic material are improved. Accordingly, this invention is very useful in the industry.

This invention has been disclosed above in the preferred embodiments, but is not limited to those. It is known to persons skilled in the art that some modifications and innovations may be made without departing from the spirit and scope of this invention. Hence, the scope of this invention should be defined by the following claims.

What is claimed is:

1. A hemostatic material, comprising a nano-fiber that comprises: a polymer, and a polypeptide having a peptide fragment of formula (1):

$$\text{-(Pro-Y-Gly)}_n\text{-} \qquad (1)$$

wherein Y represents hydroxyproline or proline, and n is an integer ranging from 5 to 9000,
wherein the polymer comprises at least one selected from the group consisting of natural collagen, polyethylene glycol, polyvinyl alcohols and polyglycolic acids, and
wherein the nano-fiber has an average length of 200 to 300 nm.

2. The hemostatic material of claim 1, wherein the content of the polypeptide in the nano-fiber ranges from 2.5 wt % to 90 wt %.

3. The hemostatic material of claim 1, wherein the nano-fiber is in a form of a nonwoven fabric.

4. The hemostatic material of claim 3 further comprising a support base material, wherein the support base material is laminated on the nonwoven fabric.

5. The hemostatic material of claim 4, wherein the support base material comprises a polyurethane.

* * * * *